(12) United States Patent
Draheim et al.

(10) Patent No.: US 7,351,470 B2
(45) Date of Patent: *Apr. 1, 2008

(54) REMOVABLE ANTIREFLECTION FILM

(75) Inventors: Erica J. Draheim, Cottage Grove, MN (US); Bettie C. Fong, Woodbury, MN (US); Bruce D. Kluge, Forest Lake, MN (US); Junkang J. Liu, Woodbury, MN (US); Pradnya V. Nagarkar, Newton, MA (US); William K. Smyth, Sudbury, MA (US)

(73) Assignee: 3M Innovative Properties Company, Saint Paul, MN (US)

( * ) Notice: Subject to any disclaimer, the term of this patent is extended or adjusted under 35 U.S.C. 154(b) by 560 days.

This patent is subject to a terminal disclaimer.

(21) Appl. No.: 10/134,150

(22) Filed: Apr. 29, 2002

(65) Prior Publication Data

US 2003/0012936 A1 Jan. 16, 2003

Related U.S. Application Data

(63) Continuation-in-part of application No. 09/026,271, filed on Feb. 19, 1998, now Pat. No. 6,464,822, and a continuation-in-part of application No. 09/924,127, filed on Aug. 7, 2001, now Pat. No. 6,660,389, which is a continuation-in-part of application No. 09/633,835, filed on Aug. 7, 2000, now Pat. No. 6,589,650.

(51) Int. Cl.
*B32B 17/10* (2006.01)

(52) U.S. Cl. .................. 428/339; 428/343; 428/354

(58) Field of Classification Search ............... 428/339, 428/212, 220, 432, 699, 701, 702, 343, 354; 359/603
See application file for complete search history.

(56) References Cited

U.S. PATENT DOCUMENTS

| 2,532,011 | A | 11/1950 | Dahlquist et al. |
| 3,498,860 | A | 3/1970 | Pickett |
| 3,793,022 | A | 2/1974 | Land et al. |
| 3,810,874 | A | 5/1974 | Mitsch et al. |
| 3,891,327 | A | 6/1975 | Welch |

(Continued)

FOREIGN PATENT DOCUMENTS

CH 400607 12/1962

(Continued)

OTHER PUBLICATIONS

Southwall Technologies, "Thin Film Coatings. . . " SID International Symposium and Exhibition, San Diego CA, May 1996.

(Continued)

*Primary Examiner*—N. Edwards

(57) ABSTRACT

An antireflection film and method of making same includes a substrate having a first surface and a second surface, an inorganic layer deposited on the first surface of the substrate, and an optically active polymer layer formed by curing a curable composition in situ on the inorganic layer, the polymer layer having a refractive index not greater than about 1.53 over the wavelength range of 400 nm to 700 nm and a thickness of from about 20 nm to about 200 nm, and an adhesive layer deposited on the second surface of the substrate.

35 Claims, 3 Drawing Sheets

U.S. PATENT DOCUMENTS

| | | | |
|---|---|---|---|
| 3,925,081 A | 12/1975 | Chiklis | |
| 3,939,019 A | 2/1976 | Pickett | |
| 4,047,804 A | 9/1977 | Stephens | |
| 4,066,814 A | 1/1978 | Chiklis | |
| 4,070,097 A | 1/1978 | Gelber | |
| 4,077,830 A | 3/1978 | Fulwiler | |
| 4,188,246 A | 2/1980 | Lipshaw | |
| 4,203,797 A | 5/1980 | Stormby | |
| 4,234,654 A | 11/1980 | Yatabe et al. | |
| 4,320,169 A | 3/1982 | Yatabe et al. | |
| 4,321,404 A | 3/1982 | Williams et al. | |
| 4,361,598 A | 11/1982 | Yoldas | |
| 4,386,130 A | 5/1983 | Hayashi et al. | |
| 4,422,721 A | 12/1983 | Hahn et al. | |
| 4,455,188 A | 6/1984 | Stormby | |
| 4,465,736 A | 8/1984 | Nishihara et al. | |
| 4,472,480 A | 9/1984 | Olson | |
| 4,567,073 A | 1/1986 | Larson et al. | |
| 4,747,674 A * | 5/1988 | Butterfield et al. | 359/590 |
| 4,765,729 A | 8/1988 | Taniguchi | |
| 4,830,910 A | 5/1989 | Larson | |
| 4,853,262 A | 8/1989 | Horie et al. | |
| 4,904,525 A | 2/1990 | Taniguchi et al. | |
| 4,907,090 A | 3/1990 | Ananian | |
| 4,940,602 A | 7/1990 | Taniguchi et al. | |
| 4,966,813 A | 10/1990 | Agou et al. | |
| 5,002,326 A | 3/1991 | Westfield et al. | |
| 5,061,769 A | 10/1991 | Aharoni | |
| 5,104,929 A | 4/1992 | Bilkadi | |
| 5,106,671 A | 4/1992 | Amberger et al. | |
| 5,118,579 A | 6/1992 | Aharoni et al. | |
| 5,139,879 A | 8/1992 | Aharoni et al. | |
| 5,171,414 A | 12/1992 | Amberger et al. | |
| 5,175,030 A | 12/1992 | Lu et al. | |
| 5,178,955 A | 1/1993 | Aharoni et al. | |
| 5,183,597 A | 2/1993 | Lu | |
| 5,198,267 A * | 3/1993 | Aharoni et al. | 427/162 |
| 5,225,244 A | 7/1993 | Aharoni et al. | |
| 5,234,748 A | 8/1993 | Demiryont et al. | |
| 5,306,758 A | 4/1994 | Pellerite | |
| 5,332,797 A | 7/1994 | Kessel et al. | |
| 5,389,438 A | 2/1995 | Miller et al. | |
| 5,392,156 A | 2/1995 | Kumagai et al. | |
| 5,409,777 A | 4/1995 | Kennedy et al. | |
| 5,449,558 A | 9/1995 | Hasegawa et al. | |
| 5,506,279 A | 4/1996 | Babu et al. | |
| 5,514,526 A | 5/1996 | Nishi et al. | |
| RE35,318 E | 8/1996 | Warman | |
| 5,648,407 A | 7/1997 | Goetz et al. | |
| 5,670,598 A | 9/1997 | Leir et al. | |
| 5,677,050 A | 10/1997 | Bilkadi et al. | |
| 5,693,366 A | 12/1997 | Mase et al. | |
| 5,712,325 A | 1/1998 | Lewis et al. | |
| 5,744,227 A | 4/1998 | Bright et al. | |
| 5,763,061 A | 6/1998 | Ochiai et al. | |
| 5,783,049 A | 7/1998 | Bright et al. | |
| 5,811,472 A | 9/1998 | Patel | |
| 5,812,312 A | 9/1998 | Lorincz | |
| 5,820,957 A * | 10/1998 | Schroeder et al. | 428/40.1 |
| 5,851,664 A | 12/1998 | Bennett et al. | |
| 5,851,674 A | 12/1998 | Pellerite et al. | |
| 5,922,787 A | 7/1999 | Kondo et al. | |
| 6,004,670 A | 12/1999 | Kobe et al. | |
| 6,059,628 A | 5/2000 | Yoo et al. | |
| 6,099,682 A | 8/2000 | Krampe et al. | |
| 6,132,861 A | 10/2000 | Kang et al. | |
| 6,238,798 B1 | 5/2001 | Kang et al. | |
| 6,245,428 B1 | 6/2001 | Port et al. | |
| 6,245,833 B1 | 6/2001 | Kang et al. | |
| 6,250,765 B1 | 6/2001 | Murakami | |
| 6,277,485 B1 | 8/2001 | Invie et al. | |
| 6,352,758 B1 | 3/2002 | Huang et al. | |
| 6,376,060 B1 * | 4/2002 | Yoshihara et al. | 428/323 |
| 6,379,788 B2 | 4/2002 | Choi et al. | |
| 6,383,620 B1 | 5/2002 | Aoyama et al. | |
| 6,392,727 B1 * | 5/2002 | Larson et al. | 349/96 |
| 6,461,709 B1 | 10/2002 | Janssen et al. | |
| 6,502,943 B2 * | 1/2003 | Nakamura et al. | 359/603 |
| 6,632,513 B1 * | 10/2003 | Choi et al. | 428/216 |
| 6,800,378 B2 * | 10/2004 | Hawa et al. | 428/688 |
| 6,815,056 B2 * | 11/2004 | Choi et al. | 428/339 |
| 6,830,348 B2 * | 12/2004 | Nakamura et al. | 359/603 |

FOREIGN PATENT DOCUMENTS

| | | |
|---|---|---|
| DE | 3637188 | 5/1988 |
| EP | 0 749 021 | 12/1996 |
| FR | 254876 | 9/1984 |
| JP | 63-248807 | 4/1987 |
| JP | 63-228101 | 9/1988 |
| JP | 04-338901 | 11/1992 |
| JP | 11-101943 | 4/1999 |
| JP | 2000/020240 | 1/2000 |
| JP | 2000-056694 | 2/2000 |
| JP | 2001-083886 | 3/2001 |
| WO | WO 99 42860 | 8/1999 |
| WO | WO 99/42860 | 8/1999 |
| WO | WO 99/53357 | 10/1999 |
| WO | WO 01 88572 | 11/2001 |
| WO | WO 01/88572 | 11/2001 |

OTHER PUBLICATIONS

International Search Report PCT/US01/24923 mailed Feb. 14, 2002.

International Search Report PCT/US01/24726 mailed Feb. 14, 2002.

PCT Search Report WO 0031570, PCT/US99/26229, dated Feb. 28, 2000.

SID 96 Applications Digest, Society for Information Display International Symposium Digest of Applications Papers, "Linear Polarizer Advancements with the Use of Hydrophobic Multilayer Thin-Film Coating Technology," M.D. Parish et al., 1996 pp. 25-28.

* cited by examiner

REMOVABLE ANTIREFLECTION FILM

CROSS-REFERENCE TO RELATED APPLICATIONS

This application is a continuation-in-part of application Ser. No. 09/026,271, filed Feb. 19, 1998, now U.S. Pat. No. 6,464,822 entitled "ANTIREFLECTION FILM", and a continuation-in-part of application Ser. No. 09/924,127, filed Aug. 7, 2001, now U.S. Pat. No. 6,660,389 entitled "INFORMATION DISPLAY PROTECTORS", which is a continuation-in-part of application Ser. No. 09/633,835, filed Aug. 7, 2000, now U.S. Pat. No. 6,589,650 entitled "MICROSCOPE COVER SLIDE MATERIALS", the disclosures of which are incorporated by reference herein.

FIELD OF THE INVENTION

This invention relates to a removable antireflection film and, in particular, to an antireflection film for information displays.

BACKGROUND OF THE INVENTION

It is advantageous to provide various articles, for example, lenses, cathode ray tubes, optical displays, window films and windshields, with antireflection films which reduce the amount of light reflected from the surface of the article and thus reduce or eliminate "ghost" images formed by such reflected light. In addition, it is beneficial to provide various articles, such as optical displays, with protective films and/or antisoiling films in order to reduce the amount of contamination or damage to the surface of the article. For example, optical displays used in devices such as personal digital assistants ("PDAs"), cell phones, touch-sensitive screens, flat panel displays and removable computer filters are frequently subjected to handling and contact with a user's face, fingers, stylus, jewelry and/or other objects. Consequently, facial oils can adversely affect contrast, color saturation or brightness of an optical display. Scratches, abrasion, smudges and stains resulting from routine use can also cause the optical display to lose resolution and clarity, and sometimes to become unreadable or inoperative.

Antireflection coatings on a substrate typically comprise a plurality of inorganic layers, for example a metal or metal oxide layer and a silica layer. (The term "silica" is used herein in accordance with its normal meaning in the antireflection art to mean a material of the formula $SiO_x$ where x is not necessarily equal to two. As those skilled in the art are aware, such silica layers are often deposited by chemical vapor deposition, vacuum deposition, or sputtering of silicon in an oxygen atmosphere, so that the material deposited does not precisely conform to the stoichiometric formula $SiO_2$ of pure silica.) Typically, one surface of a silica layer is exposed, and this exposed surface, which has a high surface energy as shown by its low contact angle with water, is highly susceptible to fingerprints and other marks. Such marks are extremely difficult to clean, often requiring the use of chemical cleaners.

An effective antireflection film is available commercially from Southwall Technologies (Palo Alto, Calif.). This material comprises a 180 µm poly(ethylene terephthalate) substrate provided with an abrasion-resistant hardcoat, and then successively with a 17 nm indium tin oxide (ITO) layer, a 23 nm silica layer, a 95 nm ITO layer, an 84 nm silica layer and finally a thin "lubrication" layer, which is formed from a fluoropolymer and is stated to improve the scratch resistance and to decrease the susceptibility of the surface to marking.

This complex film possesses excellent antireflection characteristics, but is so expensive (approximately US$10 per square foot, US$100 $m^{-2}$) as to preclude its use in many applications where antireflection films are desirable. Much of the high cost of this film can be attributed to the 95 nm ITO layer and 84 nm silica layer, since these layers are typically formed by sputtering, and the cost of a sputtered layer is directly proportional to its thickness. Furthermore, if it is desired to produce large quantities of such a complex film on a production line basis, the need for four separate sputtering stations, all of which must be maintained under high vacuum, results in a complex and costly apparatus.

It has now been found that by providing a "thick" (i.e., optically active) polymer layer of carefully controlled refractive index above an inorganic layer or layers, the thickness(es) of the inorganic layer(s) can be greatly reduced, thereby reducing the overall cost of the antireflection coating, especially when the inorganic layer(s) is/are applied by a process such as sputtering or chemical vapor deposition in which the residence time of the substrate within the coating apparatus is directly proportional to the thickness of the required layer. Also, an antireflection coating using such a thick polymer layer, which can readily be applied with good uniformity by solution or other coating techniques, has good scratch or abrasion resistance and good stain, smudge, and soil resistance.

SUMMARY OF THE INVENTION

In general, in one aspect, the invention features an antireflection film and method of making same. The antireflection film includes a substrate having a first surface and a second surface, an inorganic layer deposited on the first surface of the substrate, an optically active polymer layer formed by curing a curable composition in situ on the inorganic layer, the polymer layer having a refractive index not greater than about 1.53 over the wavelength range of 400 to 700 nm and a thickness of from about 20 to about 200 nm, and an adhesive layer deposited on the second surface of the substrate In general, in another aspect, the invention features an optical system and method of making same. The optical system includes a display device and an antireflection film disposed on at least a portion of the display device, wherein the antireflection film includes a substrate having a first surface and a second surface, an inorganic layer deposited on the first surface of the substrate, an optically active polymer layer formed by curing a curable composition in situ on the inorganic layer, the polymer layer having a refractive index not greater than about 1.53 over the wavelength range of 400 nm to 700 nm and a thickness of from about 20 nm to about 200 nm, and an adhesive layer deposited on the second surface of the substrate.

In general, in another aspect, the invention features a method for producing a stack of removable antireflection films. A plurality of antireflection films is formed by providing a substrate having a first surface and a second surface, depositing an inorganic layer on the first surface of the substrate, depositing a layer of a curable composition on the inorganic layer, and curing the deposited curable composition to form an optically active polymer layer having a thickness of from about 20 nm to about 200 nm and a refractive index not greater than about 1.53 over the wavelength range of 400 nm to 700 nm, and depositing an adhesive layer on the second surface of the substrate. The plurality of antireflection films is placed adjacent to one another wherein the adhesive layer of one antireflection film is adjacent to the polymer layer of another antireflection film.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
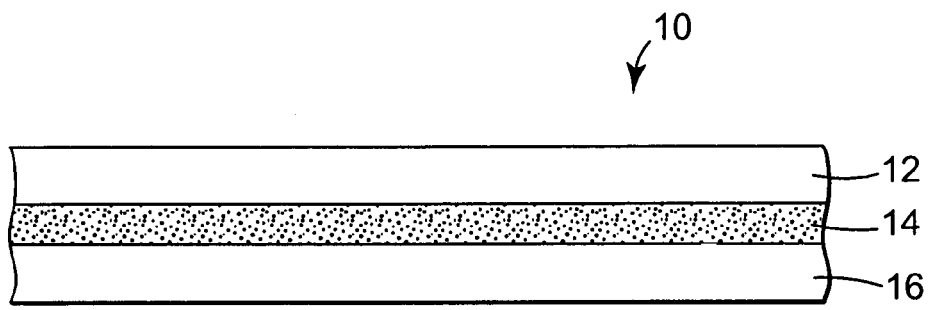
FIG. 1 is a schematic side view of a screen protector of the prior art.

The removable antireflection film of the present invention and components thereof are sometimes shown or described herein using words of orientation such as "upper", "atop", "above" or "front". These and similar terms are merely employed for convenience to refer to the general direction (with respect to the optical path through an antireflection film) towards a normal viewer of a display device. Likewise, the removable antireflection film of the present invention and components thereof are sometimes shown or described herein using words of orientation such as "lower", "beneath", "underneath" or "behind". These and similar terms are merely employed for convenience to refer to the general direction (with respect to such optical path) towards the film. As will be understood by those skilled in the art, the removable antireflection film of the present invention can be used in a variety of orientations and locations.

The antireflection film of the present invention can be used on a variety of information displays having several information display area configurations. Such displays include multi-character and especially multi-character, multi-line displays, such as liquid crystal displays ("LCDs"), plasma displays, front and rear projection displays, cathode ray tubes ("CRTs") and signage, and single-character or binary displays, such as light emitting diodes ("LEDs"). The antireflection film of the present invention is especially useful on displays whose information display area is in the form of a viewing screen having a viewing surface that is susceptible to damage and glare during normal use.

The antireflection film of the present invention can be employed in a variety of portable and non-portable information display devices including PDAs, cell phones (including combination PDA/cell phones), touch-sensitive screens, wrist watches, car navigation systems, global positioning systems, depth finders, calculators, handheld electronic game player, electronic books, CD or DVD players, projection television screens, computer monitors, notebook computer displays, instrument gauges, tablet personal computers, LCD televisions, instrument panel covers, signage such as graphic displays (including indoor and outdoor graphics), and the like. These devices can have planar viewing faces, or non-planar viewing faces such as the slightly curved face of a typical CRT. Typically the display element is located on or in close physical proximity to a viewing face of the information display device rather than being spaced an appreciable distance therefrom.

An antireflection film of the present invention can also be employed with a light polarizer, such as a linear polarizer or a circular polarizer (typically a circular polarizer is implemented as a linear polarizer in combination with a quarter-wavelength retarder). An antireflection film with a light polarizer may be employed in a variety of display devices, such as PDAs, cell phones (including combination PDA/cell phones), touch-sensitive screens, wrist watches, car navigation systems, global positioning systems, depth finders, calculators, handheld electronic game player, electronic books, CD or DVD players, projection television screens, computer monitors, notebook computer displays, instrument gauges, tablet personal computers, LCD televisions, instrument panel covers, signage such as graphic displays (including indoor and outdoor graphics), and the like.

FIG. 1 shows a screen protector 10 of the prior art typically intended for use on a display device screen. Screen protector 10 is a single sheet of vinyl film 12 coated with an adhesive 14 and adhered to a liner 16. Such screen protectors typically are sold as a set of sheets on liners, placed loosely in a box or packaged on a retail hang card. The stack is typically stored separately from the display device and must be found when the user desires to put a new screen protector on the display device. Screen protector 10 has a relatively soft surface that does not provide scratch resistance or smudge resistance, and does not reduce glare. Instead, screen protector 10 serves mainly as a sacrificial membrane that shields the top membrane of the underlying display device screen.

Figure 2:
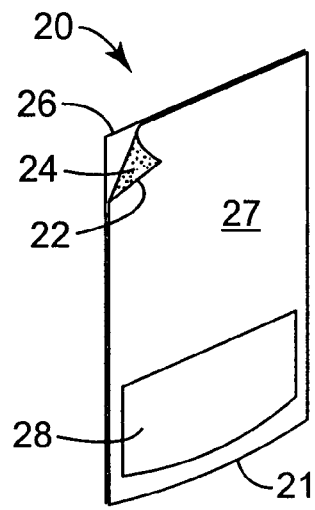
FIG. 2 is a perspective view of another screen protector of the prior art.

FIG. 2 shows another screen protector 20 of the prior art having a curved bottom edge 21 and overall dimensions suited for use on a PDA device, such as a PALM™ V PDA manufactured by Palm, Inc. Like screen protector 10, screen protector 20 is sold as a single sheet of film 22 coated with an adhesive 24 and adhered to a liner 26. However, a portion of the top surface 27 of screen protector 20 has a matte finished region 28 that provides some glare resistance and some improvement in stylus feel for the writing area on the PDA screen. Region 28 does not offer smudge or soil resistance and thus is susceptible to staining, fingerprints and marking with ink and pencil lead. The remainder of the top surface 27 of screen protector 20 is relatively soft and does not provide scratch resistance or smudge resistance.

Figure 3:
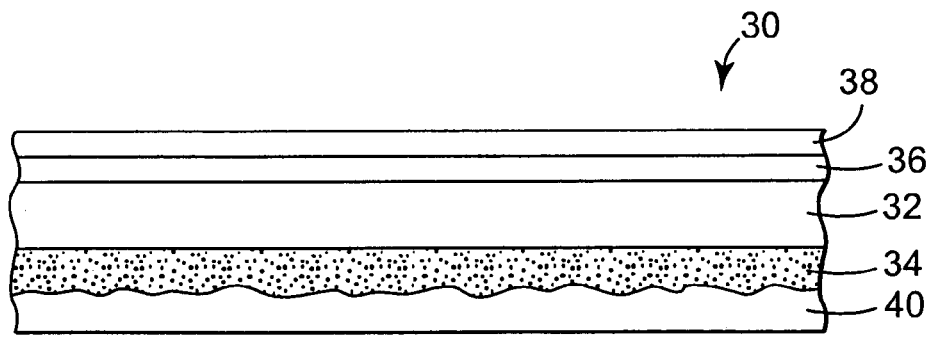
FIG. 3 is a schematic side view of an antireflection film according to an embodiment of the present invention.

FIG. 3 shows an antireflection film 30 according to an embodiment of the present invention. The antireflection film 30 comprises a substrate 32, an adhesive layer 34, an inorganic layer 36 and an outer, optically active polymer layer 38. The lower surface of substrate 32 is coated with adhesive layer 34 to which has been applied a protective liner 40. The lower surface of adhesive 34 is optionally microtextured. Microtexturing helps air bubbles escape from beneath the antireflection film 30 when the film is applied to a surface, such as a display screen, and helps to provide good optical coupling between antireflection film 30 and the surface of the device.

The upper surface of substrate 32 is coated with inorganic layer 36. Inorganic layer 36 may include one or more layers and may be formed from any of the inorganic materials hitherto used in antireflection coatings. The preferred materials for forming the inorganic layer are metal oxides, nitrides, nickel, chromium, and silica. Preferred metal oxides are indium oxide, titanium dioxide, nickel oxide, chromium oxide, cadmium oxide, gallium indium oxide, niobium pentoxide, indium tin oxide, tin dioxide, and any combination thereof, with indium tin oxide being especially preferred. Preferred nitrides are silicon nitride, titanium nitride, and a combination thereof.

Optically active polymer layer 38 is coated on inorganic layer 36 and preferably has a thickness of from about 20 to about 200 nm and a refractive index preferably not greater than about 1.53 over the visible wavelength range of 400 to 700 nm. Polymer layer 38 is preferably formed on inorganic layer 36 by depositing a layer of a curable composition and then curing this layer in situ. The relatively thick layer of curable composition required can be applied with good uniformity by solution coating or other conventional coating techniques. Also, the provision of the thick polymer layer enables the thickness, and thus the cost, of the inorganic layer to be reduced. For example, one embodiment of the invention described below comprises a 19 nm indium tin oxide layer, a 20 nm silica layer and an 85 nm polymer layer as compared to the Southwall Technology antireflection film described above. This embodiment of the invention reduces the amount of material which needs to be sputtered per unit area of the film by about 80 percent, thus reducing the cost of the film by more than 50 percent.

Figure 4:
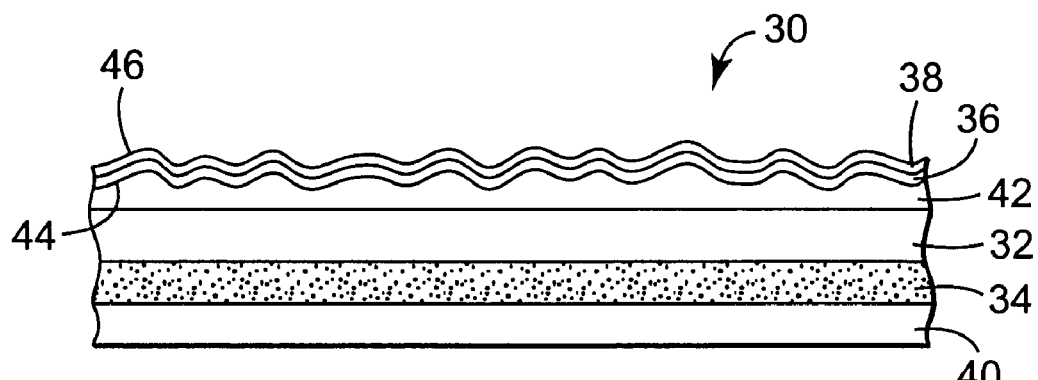
FIG. 4 is a schematic side view of another antireflection film according to an embodiment of the present invention.

FIG. 4 shows an antireflection film 30 according to another embodiment of the present invention. The lower surface of substrate 32 is coated with an adhesive layer 34 to which has been applied a protective liner 40. The lower surface of adhesive 40 is relatively smooth rather than microtextured as shown in FIG. 3. The upper surface of substrate 32 is optionally coated with a hardcoat layer 42. Hardcoat layer 42 provides scratch and abrasion resistance to antireflection film 30 to help protect the surface of a device from damage. Hardcoat layer 42 has a thickness of about 1 μm to about 15 μm, preferably from about 2 μm to about 3 μm. Hardcoat 42 may have a roughened upper surface 44. Inorganic layer 36 and polymer layer 38 are sufficiently thin so that the roughened upper surface 44 of hardcoat 42 is replicated on viewing surface 46, thus providing a matte finish to antireflection film 30 and making antireflection film 30 easier to write on. If the upper surface 44 of hardcoat 42 is substantially smooth (not shown), antireflection film 30 has a glossy finish.

Referring to FIG. 3 or FIG. 4, an optional antistatic coating (not shown) may be applied on top of polymer layer 38 or an optional antistatic agent may be included in polymer layer 38 in order to discourage dust and other contaminants from adhering to antireflection film 30. An optional louvered plastic layer (not shown) may also be applied between substrate 32 and adhesive layer 34 or may be used as the substrate in order to provide privacy and contrast enhancement. A louvered plastic layer is a thin plastic film containing closely spaced black microlouvers that control the viewing angle. The viewing angle is determined by the thickness and frequency of the microlouvers. The layer simulates a tiny Venetian blind to shield out unwanted ambient light and direct the light emitted from the displays. A suitable commercially available film is Light Control Film available from 3M Company (St. Paul, Minn.). A circular polarizer (not shown) may also be used between substrate 32 and adhesive layer 34 or may be used as the substrate. When used between the substrate and adhesive layer, substrate 32 is formed on the linear polarizer and adhesive layer 34 is formed on the quarter-wavelength retarder. When used as the substrate, inorganic layer 36 is formed on the linear polarizer and adhesive layer 34 is formed on the quarter-wavelength retarder.

Figure 5:
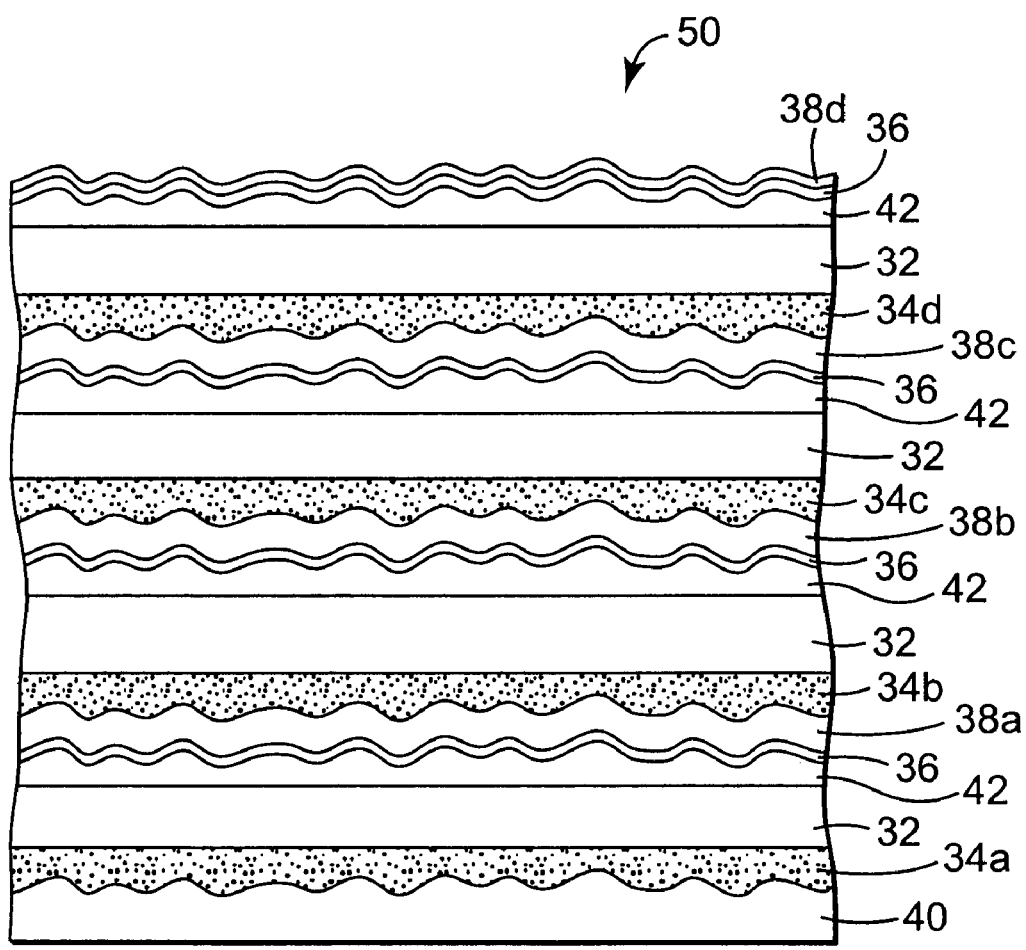
FIG. 5 is a perspective view of a stack of removable antireflection films according to an embodiment of the present invention.

FIG. 5 shows a stack 50 of removable antireflection films 30 according to an embodiment of the present invention. Stack 50 has a single liner 40 protecting adhesive layer 34a of the lowermost antireflection film 30. The remaining antireflection films 30 can be adhered to one another by pressing the bottom surface of adhesive layers 34b, 34c and 34d against the upper surface of polymer layers 38a, 38b and 38c, respectively.

Figure 6:
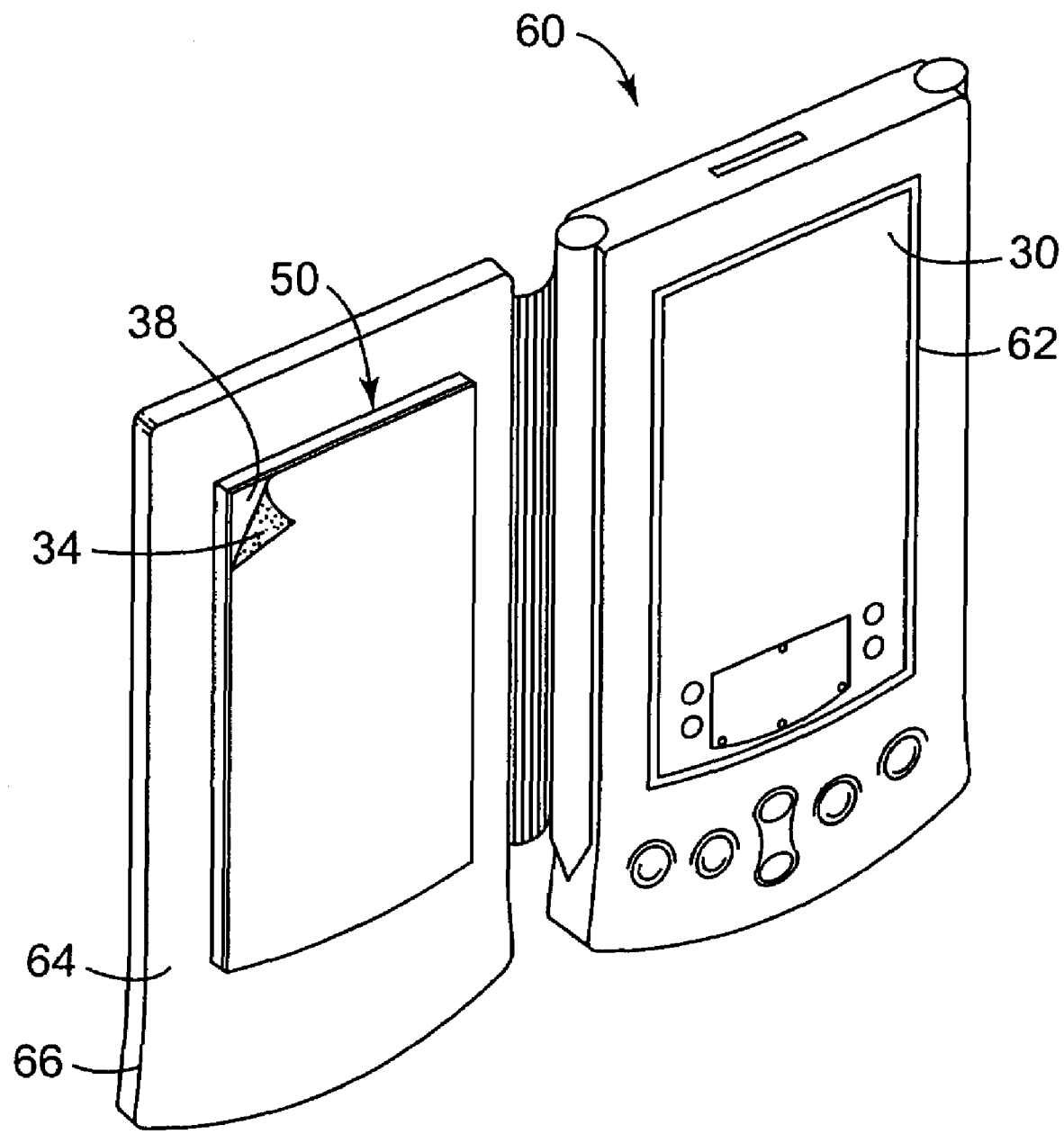
FIG. 6 is a perspective view of a PDA, the display screen being covered with an antireflection film according to an embodiment of the present invention and the inside front cover having a stack of antireflection films adhered thereto according to another embodiment of the present invention.

FIG. 6 shows a PDA 60 to which has been applied an antireflection film 30. In the case of a single antireflection film 30, a user can remove liner 40 from adhesive 34, center antireflection film 30 over display screen 62 of the PDA 60 and press film 30 into place. In the case of a stack 50 of antireflection films 30, a user can remove the uppermost antireflection film 30 from the stack 50 by peeling lower surface of adhesive layer 34 away from upper surface of polymer layer 38 and adhere film 30 to display screen 62 as described above. If the thus-applied antireflection film 30 later becomes worn or damaged, film 30 can be peeled off display screen 62 and replaced with another antireflection film 30, by either method previously described. When antireflection film 30 is used in this manner, antireflection film 30 preferably is precut to slightly undersized dimensions so that the edges of antireflection film 30 extend nearly to the perimeter of display screen 62, while still permitting film 30 to be easily removed later if desired.

A user may store a stack 50 of antireflection films 30 in any convenient location. For example, stack 50 may be adhered directly to a display device screen or to its case or cover by removing liner 40 from the stack 50 and pressing the stack in place. FIG. 6 shows a stack 50 of antireflection films 30 adhered to inside surface 64 of PDA front cover 66. Although not shown in FIG. 6, the stack could instead be adhered to the display screen of PDA 60, to the rear of PDA 60 or to any available surface of a separate PDA case. If the stack 50 contains a relatively low number of protectors (e.g., 10 or less, more preferably 5 or less), it will not unduly obscure underlying printed graphics on the front cover (such as the printed GRAFFITI™ alphabet symbol guide that is supplied with some PDAs) and will not hamper closure of a display device cover or case if applied to an inside surface thereof.

A wide variety of substrate materials can be used in the present invention. The substrate should be substantially transparent, that is, the substrate should have sufficient transparency or translucency at the intended wavelength and under the intended viewing conditions or viewing angle so that the antireflection film does not unduly impede use and viewing of the underlying display device screen. The adhesive and/or substrate may be tinted with a suitable color, such as grey or light brown, in order to impart a desired color to the antireflection film. Suitable substrate materials include thermosetting or thermoplastic polymers such as polycarbonate, poly(meth)acrylate (e.g., polymethyl methacrylate or "PMMA"), polyolefins (e.g., polypropylene or "PP"), polyurethane, polyesters (e.g., polyethylene terephthalate or "PET"), polyamides, polyimides, phenolic resins, cellulose diacetate, cellulose triacetate, polystyrene, styrene-acrylonitrile copolymers, epoxies, and the like. Typically the substrate will be chosen based in part on the desired optical and mechanical properties for the intended use. Such mechanical properties typically will include flexibility, dimensional stability and impact resistance. The substrate thickness typically also will depend on the intended use. For most applications, substrate thicknesses of less than about 0.5 mm are preferred, and more preferably about 0.02 to about 0.2 mm. Self-supporting polymeric films are preferred. Films made from polyesters such as PET or polyolefins such as PP (polypropylene), PE (polyethylene) and PVC (polyvinyl chloride) are particularly preferred. The substrate can be formed into a film using conventional filmmaking techniques such as extrusion of the substrate resin into a film and optional uniaxial or biaxial orientation of the extruded film.

The substrate may be provided with coatings on one or both surfaces to improve its hardness and scratch resistance, to improve the adhesion of the inorganic layer or the optional hardcoat layer to the substrate, or to provide any other desired properties, for example filtration of ultra-violet radiation or provision of a gas and/or moisture barrier. For example, the substrate may be treated to improve adhesion between the substrate and the inorganic layer or the optional hardcoat layer, using, e.g., physical treatment, such as corona treatment, including air or nitrogen corona, plasma, flame, or actinic radiation. If desired, an optional chemical treatment, such as a primer coating can also be applied between the substrate and the inorganic layer or hardcoat layer to increase the interlayer adhesion.

A wide variety of hardcoat materials may optionally be used in the present invention. The hardcoat layer preferably contains nanometer-sized inorganic oxide particles dispersed in a binder matrix, also referred to as "ceramers". The hardcoat may be formed by coating a curable liquid ceramer composition onto the substrate and curing the composition in situ to form a hardened film. Suitable coating methods include, for example, spin coating, knife coating, die coating, wire coating, flood coating, padding, spraying, roll coating, dipping, brushing, foam application, and the like.

A variety of inorganic oxide particles may be used in the hardcoat. The particles preferably are substantially spherical in shape and relatively uniform in size. The particles can have a substantially monodisperse size distribution or a polymodal distribution obtained by blending two or more substantially monodisperse distributions. Preferably the inorganic oxide particles are and remain substantially non-aggregated (substantially discrete), as aggregation can result in precipitation of the inorganic oxide particles or gelation of the hardcoat. Preferably the inorganic oxide particles are colloidal in size, that is, they preferably have an average particle diameter of about 0.001 to about 0.2 micrometers, more preferably less than about 0.05 micrometers, and most preferably less than about 0.03 micrometers. These size ranges facilitate dispersion of the inorganic oxide particles into the binder resin and provide ceramers with desirable surface properties and optical clarity. The average particle size of the inorganic oxide particles can be measured using transmission electron microscopy to count the number of inorganic oxide particles of a given diameter. Preferred inorganic oxide particles include colloidal silica, colloidal titania, colloidal alumina, colloidal zirconia, colloidal vanadia, colloidal chromia, colloidal iron oxide, colloidal antimony oxide, colloidal tin oxide, and mixtures thereof. The inorganic oxide particles can consist essentially of or consist of a single oxide such as silica, or can comprise a combination of oxides, such as silica and aluminum oxide, or a core of an oxide of one type (or a core of a material other than a metal oxide) on which is deposited an oxide of another type. Silica is a particularly preferred inorganic particle. The inorganic oxide particles are desirably provided in the form of a sol containing a colloidal dispersion of inorganic oxide particles in liquid media. The sol can be prepared using a variety of techniques and in a variety of forms including hydrosols (where water serves as the liquid medium), organosols (where organic liquids so serve), and mixed sols (where the liquid medium contains both water and an organic liquid), e.g., as described in U.S. Pat. Nos. 5,648,407 (Goetz et al. '407) and 5,677,050 (Bilkadi et al. '050), the disclosure of which is incorporated by reference herein. Aqueous sols of amorphous silica are particularly preferred. Preferred sols generally contain from about 2 to about 50 weight percent, preferably from about 25 to about 45 weight percent, of colloidal inorganic oxide particles based on the total weight of the sol. Preferred sols can be obtained from suppliers such as ONDEO Nalco Co. (for example, NALCO™ 1040, 1042, 1050, 1060, 2327, and 2329 colloidal silicas), Nyacol Nano Technologies, Inc. (for example, NYACOL™ AL20 colloidal alumina and NYACOL™ A1530, A1540N, and A1550 colloidal antimony pentoxides), and W. R. Grace and Co. (for example, LUDOX™ colloidal silicas). The surface of the inorganic particles can be "acrylate functionalized" as described in Bilkadi et al. '050. The sols can also be matched to the pH of the binder, and can contain counterions or water-soluble compounds (e.g., sodium aluminate), all as described in U.S. Pat. No. 6,238,798B 1 (Kang et al. '798).

The hardcoat may conveniently be prepared by mixing an aqueous sol of inorganic oxide particles with a free-radically curable binder precursor (e.g., one or more free-radically curable monomers, oligomers or polymers that can participate in a crosslinking reaction upon exposure to a suitable source of curing energy). The resulting composition usually is dried before it is applied, in order to remove substantially all of the water. This drying step is sometimes referred to as "stripping". An organic solvent can be added to the resulting ceramer composition before it is applied, in order to impart improved viscosity characteristics and assist in coating the ceramer composition onto the substrate. After coating, the ceramer composition can be dried to remove any added solvent, and then can be at least partially hardened by exposing the dried composition to a suitable source of energy in order to bring about at least partial cure of the free-radically curable binder precursor.

The hardcoat preferably contains about 10 to about 50 parts by weight, and more preferably about 25 to about 40 parts by weight of inorganic oxide particles per 100 parts by weight of the binder. More preferably the hardcoat is derived from a ceramer composition containing about 15% to about 40% acrylate functionalized colloidal silica, and most preferably about 15% to about 35% acrylate functionalized colloidal silica.

A variety of binders can be employed in the hardcoat. Preferably the binder is derived from a free-radically polymerizable precursor that can be photocured once the hardcoat composition has been coated upon the substrate. Binder precursors such as the protic group-substituted esters or amides of an acrylic acid described in U.S. Pat. No. 5,104, 929 (Bilkadi '929), or the ethylenically-unsaturated monomers described in Bilkadi et al. '050, are especially preferred. Suitable binder precursors include polyacrylic acid or polymethacrylic acid esters of polyhydric alcohols, such as diacrylic acid or dimethacrylic acid esters of diols including ethyleneglycol, triethyleneglycol, 2,2-dimethyl-1,3-propanediol, 1,3-cyclopentanediol, 1-ethoxy-2,3-propanediol, 2-methyl-2,4-pentanediol, 1,4-cyclohexanediol, 1,6-hexamethylenediol, 1,2-cyclohexanediol, 1,6-cyclohexanedimethanol, resorcinol, pyrocatechol, bisphenol A, and bis(2-hydroxyethyl) phthalate; triacrylic acid or trimethacrylic acid esters of triols including glycerin, 1,2,3- propanetrimethanol, 1,2,4-butanetriol, 1,2,5-pentanetriol, 1,3,6,-hexanetriol, 1,5,10-decanetriol, pyrogallol, phloroglucinol, and 2-phenyl-2,2-methylolethanol; tetraacrylic acid or tetramethacrylic acid esters of tetraols including 1,2,3,4-butanetetrol, 1,1,2,2,-tetramethylolethane, 1,1,3,3,-tetramethylolpropane, and pentaerythritol tetraacrylate; pentaacrylic acid or pentamethacrylic acid esters of pentols including adonitol; hexaacrylic acid or hexamethacrylic acid esters of hexanols including sorbitol, dipentaerythritol, dihydroxy ethyl hydantoin; and mixtures thereof. The binder can also be derived from one or more monofunctional monomers as described in Kang et al. '798. Preferably the binder comprises one or more N,N-disubstituted acrylamide and or N-substituted-N-vinyl-amide monomers as described in Bilkadi et al. '050. More preferably the hardcoat is derived from a ceramer composition containing about 20% to about 80% ethylenically unsaturated monomers and about 5% to about 40% N,N-disubstituted acrylamide monomer or N-substituted-N-vinyl-amide monomer, based on the total weight of the solids in the ceramer composition.

Preferably the inorganic particles, binder and any other ingredients in the hardcoat are chosen so that the cured hardcoat has a refractive index close to that of the substrate. This can help reduce the likelihood of Moiré patterns or other visible interference fringes.

As mentioned above, the hardcoat can be formed from an aqueous coating composition that is stripped to remove water prior to coating, and optionally diluted with a solvent to assist in coating the composition. Those skilled in the art will appreciate that selection of a desired solvent and solvent level will depend on the nature of the individual ingredients in the hardcoat and on the desired substrate and coating conditions.

The hardcoat can be crosslinked with various agents to increase the internal cohesive strength or durability of the hardcoat. Preferred crosslinking agents have a relatively large number of available functional groups, and include tri and tetra-acrylates, such as pentaerythritol triacrylate and pentaerythritol tetraacrylate. When used, the crosslinking agent preferably is less than about 60 parts, and more preferably about 30 to about 50 parts by weight per 100 parts by weight of the binder.

Those skilled in the art will also appreciate that the hardcoat can contain other optional adjuvants, such as surface treatment agents, surfactants, antistatic agents (e.g., conductive polymers), leveling agents, initiators (e.g., photoinitiators), photosensitizers, UV absorbers, stabilizers, antioxidants, fillers, lubricants, pigments, dyes, plasticizers, suspending agents and the like.

If the hardcoat is prepared by combining an aqueous sol of colloidal inorganic oxide particles with the binder precursor, then preferably the sol has a pH such that the particles have a negative surface charge. For example, if the inorganic particles are predominantly silica particles, the sol preferably is alkaline with a pH greater than 7, more preferably greater than 8, and most preferably greater than 9. Preferably the sol includes ammonium hydroxide or the like so that $NH_4^+$ is available as a counter cation for particles having a negative surface charge. If surface treatment of the colloidal inorganic oxide particles is desired, a suitable surface treatment agent can be blended into the sol, e.g., as described in U.S. Pat. No. 6,245,833 B1 (Kang et al. '833), the disclosure of which is incorporated by reference herein. The free-radically curable binder precursor is then added to the ceramer composition. The ceramer composition is stripped to remove substantially all of the water. For example, removing about 98% of the water, thus leaving about 2% water in the ceramer composition, has been found to be suitable. As soon as substantially all of the water is removed, an organic solvent of the type described in Kang et al. '798 preferably is added in an amount such that the ceramer composition includes from about 5% to about 99% by weight solids (preferably about 10% to about 70%). After adding the solvent, the low surface energy fluorinated compound can be added if a blended hardcoat is desired, followed by addition of any other desired adjuvants.

After coating, the solvent, if any, is flashed off with heat, vacuum, and/or the like. The coated ceramer composition is then cured by irradiation with a suitable form of energy, such as heat energy, visible light, ultraviolet light or electron beam radiation. Irradiating with ultraviolet light in ambient conditions is presently preferred due to the relative low cost and speed of this curing technique. As mentioned previously, the hardcoat surface may be roughened or textured to provide a matte surface. This can be accomplished in a variety of ways that will be familiar to those skilled in the art, including embossing the hardcoat with a suitable tool that has been bead-blasted or otherwise roughened, by adding a suitable small particle filler such as silica sand or glass beads to the hardcoat, or by carrying out the curing of the hardcoat against a suitable roughened master.

As will be apparent to those skilled in thin film optics and the design of antireflection coatings, the thickness of inorganic layer 36 and polymer layer 38 in the present invention should be correlated so that the total thickness of these layers is approximately $\lambda/4$ of the center of the wavelength range for a refractive index of preferably not greater than 1.53, e.g., the total thickness should be approximately 135-145 nm when antireflection characteristics are desired over the entire visible range of 400 to 700 nm. Also, the thickness of the inorganic layer and the polymer layer can be adjusted relative to one another to produce minimum reflectivity from the composite film.

In one embodiment of the present invention, the inorganic layer is a metal oxide layer and has a thickness of about 10 nm to about 30 nm, desirably about 17 nm to about 23 nm, while the accompanying polymer layer has a thickness of about 80 nm to about 150 nm, desirably about 110 nm to about 130 nm. This embodiment combines low production cost with good antireflection properties.

In another embodiment of the present invention, inorganic layer 36 comprises a first metal oxide layer, a silica layer deposited on the first metal oxide layer, and a second metal oxide layer deposited on the silica layer. Polymer layer 38 is then deposited on the second metal oxide layer. In this structure, the first metal oxide layer desirably has a thickness of from about 20 nm to about 35 nm, preferably about 25 nm to 30 nm, the silica layer desirably has a thickness of from about 10 to about 25 nm, preferably about 15 nm to about 20 nm, the second metal oxide layer desirably has a thickness of from about 50 nm to about 100 nm, preferably about 65 nm to about 80 nm, and the polymer layer desirably has a thickness of from about 70 nm to about 120 nm, preferably about 85 nm to about 100 nm. This preferred three inorganic layer structure provides antireflection performance substantially equal to that of the Southwall Technology four-inorganic-layer structure discussed above, while still providing a substantial reduction in production costs, since the thick silica layer, the ITO layer, and the thin lubrication layer of the four-inorganic-layer structure are eliminated.

In another embodiment of the present invention, inorganic layer 36 comprises a metal oxide layer and a silica layer deposited on the metal oxide layer. Polymer layer 38 is then deposited on the silica layer. In such a two inorganic layer structure, the metal oxide layer desirably has a thickness of from about 10 nm to about 30 nm, preferably about 10 nm to about 20 nm, the silica layer desirably has a thickness of from about 10 nm to about 120 nm, preferably about 10 nm to about 50 nm, and the polymer layer desirably has a thickness of from about 50 nm to about 130 nm, preferably about 60 nm to about 100 nm.

Although other techniques, for example e-beam and thermal evaporation may be employed to deposit the inorganic layer(s) of the present invention, the layer(s) are preferably deposited by sputtering or by chemical vapor deposition, with dc sputtering being especially preferred, although RF, magnetron and reactive sputtering and low-pressure, plasma-enhanced and laser-enhanced chemical vapor deposition may also be used. Depending on the substrate used, the deposition of the layer(s) should be effected at a temperature which does not cause damage to the substrate, with the temperature limit varying with the exact substrate material employed.

As previously mentioned, the polymer layer of the present invention preferably has a refractive index not greater than about 1.53 over the wavelength range of 400 nm to 700 nm and a thickness of from about 20 nm to about 200 nm. The preferred thickness range for polymer layer is about 50 nm to about 130 nm, preferably about 60 nm to about 100 nm. Polymer layers having a thickness within these ranges are readily prepared by depositing a solution of an appropriate curable material in an organic solvent using conventional solution coating techniques, for example slot coating, removing the solvent and curing the resultant layer of curable material.

It is desirable to keep the refractive index of the polymer layer as low as possible consistent with other acceptable properties for this layer, especially hardness and scratch and stain resistance. The polymer should also be resistant to cleaning solvents which may be used on the film, for example ethyl alcohol, aqueous ammonia, acetone, gasoline and isopropanol, and food and cosmetic items, for example peanut butter and lipstick with which polymer layer may come into contact. Finally, polymer layer 38 should also have good durability, as measured, for example by the polymer layer's ability to withstand rubbing with steel wool. Desirably, the polymer layer has a refractive index below about 1.50 over the entire visible range of 400 nm to 700 nm. To provide a suitably low refractive index, the curable composition used to form polymer layer 38 comprises a polymer of a fluoroalkene, for example poly(vinylidene fluoride) or a vinylidene fluoride/tetrafluoroethylene copolymer, such as the material sold under the trademark "KYNAR" by Atofina Chemicals, Inc. (Philadelphia, Pa.). However, since a polymer layer consisting only of a fluoroalkene polymer will typically be too soft to give good scratch protection, it is also desirable that the curable composition include an acrylate with silicone or methacrylate polymer, such as the material "ELVACITE 2041" available from ICI Americas, Inc. (Wilmington, Del.) or that sold under the trademark "ACRYLOID A21" by Rohm and Haas Co. (Philadelphia, Pa.). To promote cross-linking within the polymer layer, and thus increase the hardness of this layer, it is advantageous to include a polyfunctional acrylate monomer ("polyfunctional" being used herein in its conventional sense to denote a material having a functionality of 3 or higher) in the curable composition. A specific preferred polyfunctional acrylate monomer is SARTOMER™ SR399 by Sartomer Company, Inc. (Exton, Pa.). This material is stated by the manufacturer to be dipentaerythritol pentaacrylate. To improve the stain resistance of the polymer layer, it is advantageous to include a silicone acrylate monomer, such as TegoRad 2500 available from Goldschmidt AG (Essen, Germany).

It is well known to those skilled in polymer science that most polymers have a negative dispersion in the visible range, i.e., their refractive index at 700 nm is smaller than their refractive index at 400 nm. Calculations show that such negative dispersion adversely affects the antireflection properties of the film and hence it is desirable to reduce such negative dispersion as far as possible. The aforementioned KYNAR™ polymer has a low refractive index and small negative dispersion, which render it very suitable for use in the present curable composition. While the desirability of a fluoroalkene polymer to provide low refractive index in the polymer layer and for an acrylate or methacrylate crosslinker to provide hardness in the same layer might suggest that the properties of the polymer layer must inevitably involve a compromise between the two properties, it has been found that, if the formulation of the curable composition is carefully chosen, segregation of material occurs spontaneously during curing, resulting in a polymer layer having an outer portion enriched in the acrylate or methacrylate polymer (and thus of enhanced hardness and stain resistance) and an inner portion enriched in the fluoroalkene polymer (and thus of reduced refractive index). An additional benefit of such segregation of acrylate or methacrylate polymer material during curing is that it enables the cross-linking to occur in an oxygen-containing atmosphere, such as air, thereby avoiding the need for a nitrogen blanket as is customary during thin film ultra-violet curing, and thus reducing the cost of manufacture of the antireflection film. However, a nitrogen atmosphere may still be used if desired.

The curable composition may be cured by any conventional method, but is desirably cured by a free radical curing, which may be initiated either thermally or by ultra-violet radiation, although the latter is generally preferred. Persons skilled in polymer technology will be familiar with appropriate initiators, oxygen scavengers and other components useful in such free radical curing. However, it should be noted that, because of the extreme thinness of the polymer layer desired in the present process, the type and proportion of initiator(s) required may differ from typical formulations intended for production of thicker polymer layers.

As previously mentioned, antireflection film 30 includes an adhesive on the backside of the substrate. Preferably the adhesive is transparent or sufficiently translucent so that it will not unduly hamper viewing of an underlying display device. The adhesive may be derived from a natural product (e.g., a rubber-base adhesive) or may be a synthetic material such as a homopolymer, random copolymer, graft copolymer, or block copolymer. The adhesive may be crosslinked or uncrosslinked, and if desired can have pressure-sensitive properties. An accepted quantitative description for pressure sensitive adhesives (PSAs) is given by the Dahlquist criterion, which indicates that materials having a storage modulus (G') of less than about $3 \times 10^5$ Pascals (measured at 10 radians/second at room temperature, about 20° C. to 22° C.) have pressure sensitive adhesive properties while materials having a G' greater than about $3 \times 10^5$ Pascals do not and are referred to herein as non-pressure sensitive adhesives. Non-pressure sensitive adhesives are preferred, especially those that provide selective adhesion, e.g., adhesives that have low tack or are non-tacky with respect to skin but have high tack with respect to a targeted surface such as the surface of a display. Display elements coated with such non-pressure sensitive selective adhesives can be easily handled and applied to a display surface, and can be cleanly removed if needed. Suitable low tack or non-tacky adhesives include those described in U.S. Pat. No. 5,389,438 (Miller et al.), U.S. Pat. No. 5,851,664 (Bennett et al.), U.S. Pat. No. 6,004,670 (Kobe et al.) and U.S. Pat. No. 6,099,682 (Krampe et al.).

Thermoplastic block copolymer elastomers (copolymers of segmented A and B blocks or segments, displaying both thermoplastic and elastomeric behavior) are especially preferred. Useful thermoplastic block copolymer elastomers include multi-block copolymers having radial, linear A-B diblock, and linear A-B-A triblock structures, as well as blends of such copolymers. Suitable commercially available thermoplastic block copolymer elastomers include the SOLPRENE™ family of materials (Philips Petroleum Co.), the FINAPRENE™ family of materials (FINA), the TUFPRENE™ and ASAPRENE™ family of materials (Asahi), the STEREON™ family of materials (Firestone Synthetic Rubber & Latex Co.), the EUROPRENE SOL T™ family of materials (Enichem), the VECTOR™ family of materials (Dexco Polymers), and the CARIFLEX TR™ family of materials (Shell Chemical Co.). Other suitable adhesive materials include highly crosslinked acrylic adhesives, synthetic block copolymer elastomers, silicone elastomers, acrylate elastomers, silicone polyurea elastomers such as are described in U.S. Pat. No. 5,670,598 (Leir et al.), the SEPTON™ family of materials (Kuraray Co. Ltd.) and the KRATON™ family of materials (Kraton Polymers) such as KRATON D-1101, D-1102, D-1107, D-1111, D-1112, D-1113, D-1114PX, D-1116, D-1117, D-1118, D-1119, D-1122X, D-1124, D-1125PX, D-1160, D-1165, D-1161, D-1184, D-1193, D-1300, D-1320X, D-4141, D-4158, D-4433, RP-6485, RP-6409, RP-6614, RP-6906, RP-6912, G-1650, G-1651, G-1652, G-1654, G-1657, G-1701, G-1702, G-1726, G-1730, G-1750, G-1765, G-1780, FG-1901, FG-1921, FG-1924, and TKG-101. Mixtures of adhesive materials can also be used.

The adhesive (or a liner that protects the adhesive from contamination and bears against the adhesive) can optionally be microtextured to provide air bleeding and easy handling features (as described, for example, in U.S. Pat. No. 6,197,397). Typically the adhesive layer of a single sheet or the lowermost layer of a stack of sheets will be covered by a liner. If the adhesive is a tacky adhesive, then the liner preferably has a release coating on the side facing the adhesive, such as a silicone release coating. If the adhesive has low tack or is non-tacky, then a liner made of plain paper or other low surface energy material without a release coating may suffice.

Antireflection films 30 can be converted (using techniques that will be familiar to those skilled in the art) so that they will fit the display area of a desired display device. Suitable conversion techniques include die cutting, slitting and laser cutting.

To further illustrate the present invention, the following Example is provided, but the present invention is not to be construed as being limited thereto. Unless otherwise indicated, all parts and percentages are by weight.

EXAMPLE 1

A poly(ethylene terephthalate) (PET) film (approximately 5 mils thick) with a matte hardcoat was purchased from Kimoto Tech, Inc. (Cedartown, Ga.). A 19 nm layer of indium tin oxide (ITO) and a 20 nm layer of $SiO_x$ was then deposited on top of the hardcoat surface of the PET film by direct current sputtering. A coating fluid was prepared by mixing three solutions together. Table 1 shows the chemical composition of the three solutions and the resulting coating fluid.

TABLE 1

| Material | Solution 1 | Solution 2 | Solution 3 | Coating Fluid |
| --- | --- | --- | --- | --- |
| methyl ethyl ketone (wt %) | 17.224 | 97.615 | 96.088 | 19.750 |
| 2-Pentanone (wt %) | 40.764 | | | 39.500 |
| cyclohexanone (wt %) | 40.794 | | | 39.500 |
| Kynar 7201 (wt %) | 0.645 | | | 0.625 |
| Paraloid A-21 (wt %) | 0.052 | | | 0.050 |
| Sartomer SR399 (wt %) | 0.387 | | | 0.375 |
| Sartomer CD9051 (wt %) | 0.077 | | | 0.075 |
| TegoRad 2500 (wt %) | 0.026 | | | 0.025 |
| Silquest A-174 (wt %) | | 2.385 | | 0.038 |
| KIP 100F (wt %) | | | 3.912 | 0.063 |
| % Solids (wt %) | 1.187 | 2.385 | 3.912 | 1.251 |

Kynar 7201 is available from Atofina Chemical, Inc. (Philadelphia, Pa.), Paraloid A-21 (100%) Resin (Acryloid A-21) is available from Rhom & Haas Co. (Philadelphia, Pa.), Sartomer SR399, Sartomer CD9051, and Esacure Kip 100F are available from Sartomer Company Inc. (Exton, PA), Silane A-174 (silquest A-174) is available from OSi Specialties, Inc. (Danbury, Conn.), and TegoRad 2500 is available from Goldschmidt AG (Essen, Germany).

The coating fluid was deposited on top of the sputtered layers by die coating. The solvent in the coating fluid was evaporated by passing the film through a 40 ft long floatation oven at approximately 30 ft/min at a temperature of 120° F. with an oven nozzle air velocity of approximately 8000-10000 ft/min. The film was then cured in an ultra-violet lamp chamber under an inert atmosphere. The resulting polymer coating thickness was approximately 90-100 nm.

A thermoplastic block copolymer was coated on the bottom of the PET substrate on the surface opposite the hardcoat layer, ITO and SiOx layers, and the polymer layer using a knife coater with an 8 mil gap setting. The thermoplastic block copolymer coating solution had a chemical composition of 28% Kraton G-1657 and 72% toluene. Kraton G-1657 is available from Kraton Polymers (Westhollow, Tex.). The thermoplastic block copolymer was then dried in an oven at 45° C. for 20 minutes.

A silicon-coated PET release liner purchased from Loparex Inc. (Willowbrook, Ill.) was laminated to the dried thermoplastic block copolymer with a hand roller. The antireflection film sample was adhered to a glass slide whose backside had been coated with black tape. Table 2 summarizes the resulting properties for an antireflection film made according to an embodiment of the present invention.

TABLE 2

| Property | Value |
| --- | --- |
| 1st Surface Reflection (450 nm-650 nm) | 1.43% |
| Total Reflection (450 nm-650 nm) | 4.61% |
| Transmission | 95.7% |
| Haze | 5.6% |
| Pencil hardness | 3H |

TABLE 2-continued

| Property | Value |
| --- | --- |
| Durability | >40 dry rubs |
| Peel strength, glass | 13 g/1 inch strip |
| Peel strength, Palm V | 6 g/0.5 inch strip |

The reflectance was evaluated using a spectrophotometer. Total reflection and first surface reflection measurements were made and recorded as the percent of incident illumination. Average visible photopic light transmittance was evaluated using a HAZE-GARD PLUS™ transmission measurement device manufactured by BYK-Gardner, USA (Columbia, Md.).

Pencil hardness was measured by using a series of pencils of increasing hardness values ranging from 2H-6H. The pencils were fastened in a handheld rolling test stand under a 1 kg applied load and rolled across the coated substrates for each tested pencil hardness. The coatings were rated based on the highest pencil hardness that did not scratch the coating.

Durability was measured by using a 200 g weight wrapped with Grade 0000 steel wool. The wool was rubbed several times back and forth across the coated substrate. Periodically, the rubbing was halted and an attempt was made to write on the rubbed surface using a black SHARPIE™ fine point permanent marker manufactured by Sanford Corp. (Bellwood, Ill.).

Peel strength was measured by using strips of the antireflection film with the adhesive side placed on a glass surface and on a display surface of a Palm V™ manufactured by Palm, Inc. (Santa Clara, Calif.). The strips were allowed to sit for 10 minutes before they were peeled off with a peel tester operated at 90 in/min peel rate, 180 degree peel.

Various modifications and alterations of this invention will be apparent to those skilled in the art without departing from the scope and spirit of this invention. This invention should not be restricted to that set forth herein for illustrative purposes only.

What is claimed is:

1. An antireflection film comprising:
a substrate having a first surface and a second surface;
an inorganic layer deposited on the first surface of the substrate;
an optically active polymer layer formed by curing a curable composition in situ on the inorganic layer, the polymer layer having a refractive index not greater than about 1.53 over the wavelength range of 400 nm to 700 nm and a thickness of from about 20 run, to about 200 nm; and
an adhesive layer deposited on the second surface of the substrate.

2. The antireflection film of claim 1 wherein the inorganic layer comprises a material selected from the group consisting of a metal oxide, a nitride, nickel, chromium, silica or any combination thereof.

3. The antireflection film of claim 2 wherein the metal oxide is selected from the group consisting of indium oxide, titanium dioxide, nickel oxide, chromium oxide, cadmium oxide, gallium indium oxide, niobium pentoxide, indium tin oxide, tin dioxide, or any combination thereof.

4. The antireflection film of claim 3 wherein the metal oxide layer has a thickness of from about 10 to about 30 nm and the polymer layer has a thickness of from about 80 nm to about 150 nm.

5. The antireflection film of claim 4 wherein the metal oxide layer has a thickness of from about 17 nm to about 23 nm and the polymer layer has a thickness of from about 110 nm to about 130 nm.

6. The antireflection film of claim 2 wherein the nitride is selected from the group consisting of silicon nitride, titanium nitride, or a combination thereof.

7. The antireflection film of claim 2 wherein the inorganic layer comprises a first metal oxide layer, a silica layer, and a second metal oxide layer, wherein the silica layer is disposed between the first metal oxide layer and the second metal oxide layer and wherein the first metal oxide layer is deposited on the first surface of the substrate.

8. The antireflection film of claim 7 wherein the first metal oxide layer has a thickness of from about 20 nm to about 35 nm, the silica layer has a thickness of from about 10 nm to about 25 nm, the second metal oxide layer has a thickness of from about 50 nm to about 100 nm and the polymer layer has a thickness of from about 70 nm to about 120 nm.

9. The antireflection film of claim 8 wherein the first metal oxide layer has a thickness of from about 25 nm to about 30 nm, the silica layer has a thickness of from about 15 nm to about 20 nm, the second metal oxide layer has a thickness of from about 65 nm to about 80 nm and the polymer layer has a thickness of from about 85 nm to about 100 nm.

10. The antireflection film of claim 2 wherein the inorganic layer comprises a metal oxide layer and a silica layer, wherein the metal oxide layer is deposited on the first surface of the substrate and the silica layer is deposited on the metal oxide layer.

11. The antireflection film of claim 10 wherein the metal oxide layer has a thickness of from about 10 nm to about 30 nm, the silica layer has a thickness of from about 10 nm to about 120 nm and the polymer layer has a thickness of from about 50 nm to about 130 nm.

12. The antireflection film of claim 11 wherein the metal oxide layer has a thickness of from about 10 nm to about 20 nm, the silica layer has a thickness of from about 10 nm to about 50 nm, and the polymer layer has a thickness of from about 60 nm to about 100 nm.

13. The antireflection film of claim 1 wherein the polymer layer has a refractive index not greater than about 1.50 over the wavelength range of 400 nm to 700 nm.

14. The antireflection film of claim 1 wherein the polymer layer comprises repeating units derived from a fluoroalkene, an acrylate with silicone, a methacrylate, a polyfunctional acrylate monomer, or any combination thereof.

15. The antireflection film of claim 1 wherein the polymer layer comprises repeating units derived from a fluoroalkene and repeating units derived from an acrylate with silicone and wherein the polymer layer has an outer portion enriched in the acrylate with silicone and an inner portion enriched in the fluoroalkene.

16. The antireflection film of claim 1 wherein the polymer layer comprises repeating units derived from a fluoroalkene and repeating units derived from a methacrylate and wherein the polymer layer has an outer portion enriched in the methacrylate and an inner portion enriched in the fluoroalkene.

17. The antireflection film of claim 1 wherein the polymer layer further comprises an antistatic agent.

18. The antireflection film of claim 1 further comprising an antistatic coating disposed on the polymer layer.

19. The antireflection film of claim 1 further comprising a hardcoat layer disposed between the first surface of the substrate and the inorganic layer.

20. The antireflection film of claim 19 wherein the hardcoat layer is microtextured.

21. The antireflection film of claim 19 wherein the hardcoat layer has a thickness of from about 1 μm to about 15 μm.

22. The antireflection film of claim 19 wherein the hardcoat layer comprises colloidal inorganic oxide particles dispersed in a free-radically cured binder.

23. The antireflection film of claim 22 wherein the colloidal inorganic oxide particles comprise colloidal silica particles.

24. The antireflection film of claim 22 wherein the binder is selected from the group consisting of copolymerizable free-radically curable monomers, oligomers, polymers or any combination thereof.

25. The antireflection film of claim 22 wherein the binder comprises a conductive polymer.

26. The antireflection film of claim 1 wherein the substrate is a thermosetting polymer, a thermoplastic polymer, or a combination thereof.

27. The antireflection film of claim 26 wherein the substrate is polyethylene terephthalate.

28. The antireflection film of claim 1 wherein the substrate is a louvered plastic film.

29. The antireflection film of claim 1 further comprising a louvered plastic layer disposed between the second surface of the substrate and the adhesive layer.

30. The antireflection film of claim 1 wherein the substrate is a circular polarizer comprising a linear polarizer and a quarter-wavelength retarder, wherein the inorganic layer is deposited on the linear polarizer and the adhesive layer is deposited on the quarter-wavelength retarder.

31. The antireflection film of claim 1 further comprising a circular polarizer disposed between the second surface of the substrate and the adhesive layer, wherein the circular polarizer comprises a linear polarizer and a quarter-wavelength retarder and wherein the linear polarizer is adjacent to the second surface of the substrate and the quarter-wavelength retarder is adjacent to the adhesive layer.

32. The antireflection film of claim 1 further comprising a protective liner deposited on the adhesive layer.

33. The antireflection film of claim 1 wherein the adhesive layer is microtextured.

34. The antireflection film of claim 1 wherein the adhesive layer comprises a non-pressure sensitive adhesive.

35. The antireflection film of claim 34 wherein the non-pressure sensitive adhesive is a thermoplastic block copolymer elastomer.

* * * * *

UNITED STATES PATENT AND TRADEMARK OFFICE
CERTIFICATE OF CORRECTION

PATENT NO. : 7,351,470 B2  
APPLICATION NO. : 10/134150  
DATED : April 1, 2008  
INVENTOR(S) : Erica J. Draheim Page 1 of 1

It is certified that error appears in the above-identified patent and that said Letters Patent is hereby corrected as shown below:

Column 2  
Line 42, After "substrate" insert -- . --.

Column 8  
Line 24, Delete "6,238,798B 1" and insert -- 6,238,798 B1 --, therefor.

Column 9  
Line 13, Delete "and or" and insert -- and/or --, therefor.

Column 14  
Line 27, Delete "Rhom" and insert -- Rohm --, therefor.  
Line 44, Delete "SiOx" and insert -- $SiO_x$ --, therefor.

Column 15  
Line 51, In Claim 1, delete "20 run," and insert -- 20 nm --, therefor.

Column 17  
Line 13, In Claim 24, after "is" insert -- a material --.

Signed and Sealed this

Twenty-sixth Day of August, 2008

JON W. DUDAS  
*Director of the United States Patent and Trademark Office*